US006562038B1

(12) United States Patent
Morrison

(10) Patent No.: US 6,562,038 B1
(45) Date of Patent: May 13, 2003

(54) SPINAL IMPLANT CONNECTION ASSEMBLY

(75) Inventor: Matthew M. Morrison, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/526,104

(22) Filed: Mar. 15, 2000

(51) Int. Cl.$^7$ .............................................. A61B 17/70
(52) U.S. Cl. ............................. 606/61; 606/60; 606/72
(58) Field of Search ............................ 606/60, 61, 72, 606/73

(56) References Cited

U.S. PATENT DOCUMENTS

| | | | | |
|---|---|---|---|---|
| 4,987,892 A | * | 1/1991 | Krag et al. ................... | 606/61 |
| 5,002,542 A | * | 3/1991 | Frigg ........................... | 606/61 |
| 5,344,422 A | | 9/1994 | Frigg | |
| 5,352,226 A | * | 10/1994 | Lin ............................... | 606/61 |
| 5,380,323 A | | 1/1995 | Howland | |
| 5,584,831 A | | 12/1996 | McKay | |
| 5,591,165 A | | 1/1997 | Jackson | |
| 5,613,968 A | * | 3/1997 | Lin ............................... | 606/61 |
| 5,643,263 A | * | 7/1997 | Simonson ..................... | 606/61 |
| 5,643,264 A | * | 7/1997 | Sherman et al. .............. | 606/61 |
| 5,645,544 A | | 7/1997 | Tai et al. | |
| 5,709,685 A | | 1/1998 | Dombrowski et al. | |
| 5,810,816 A | | 9/1998 | Roussouly et al. ............ | 606/61 |
| 5,879,351 A | * | 3/1999 | Viart ............................ | 606/61 |
| 5,885,285 A | | 3/1999 | Simonson ..................... | 606/61 |
| 5,938,663 A | * | 8/1999 | Petreto ......................... | 606/61 |
| 5,947,965 A | | 9/1999 | Bryan | |
| 5,947,967 A | | 9/1999 | Barker | |
| 6,027,533 A | * | 2/2000 | Olerud ......................... | 623/17 |
| 6,030,388 A | * | 2/2000 | Yoshimi et al. ............... | 606/61 |
| 6,083,226 A | * | 7/2000 | Fiz ............................... | 606/61 |
| 6,086,588 A | | 7/2000 | Ameil et al. | |
| 6,106,526 A | * | 8/2000 | Harms et al. .................. | 606/61 |
| 6,123,706 A | * | 9/2000 | Lange .......................... | 606/61 |
| 6,183,473 B1 | * | 2/2001 | Ashman ....................... | 606/61 |
| 6,187,005 B1 | * | 2/2001 | Brace et al. ................... | 606/61 |
| 6,248,107 B1 | | 6/2001 | Foley et al. | |

FOREIGN PATENT DOCUMENTS

| | | |
|---|---|---|
| EP | 0 553 424 | 11/1992 |
| EP | 0 786 235 B1 | 1/1997 |
| EP | 0 786 235 A2 | 7/1997 |
| EP | 0 982 007 A2 | 3/2000 |
| FR | 2 692 471 A | 12/1993 |
| FR | 2 806 902 A1 | 10/2001 |
| WO | WO 01/67972 A3 | 9/2001 |

* cited by examiner

Primary Examiner—Kevin Shaver
Assistant Examiner—Michael B. Priddy
(74) Attorney, Agent, or Firm—Woodard, Emhardt, Naughton, Moriarty & McNett LLP

(57) ABSTRACT

A variable angle connection between a spinal rod and a vertebral anchor with a clevis to attach to the vertebral anchor, permitting the vertebral anchor to be longitudinally offset from the connecting point on the rod. The connection assembly has a bolt with a stop disposed near one end of the bolt and an aperture for receiving a portion of the spinal implant rod at the other end. The assembly also has a clevis. The clevis defines a bore to hold a portion of the vertebral anchor and the ears of the clevis have holes through which the bolt is located with the ears positioned between the stop and aperture of the bolt. The assembly also has a rod interface washer positioned over a portion of the bolt, between the aperture of the bolt and the inside ear of the clevis. The rod interface washer is partly movable between the aperture of the bolt and the clevis, but the washer is fixed against rotating in relation to the bolt. Finally, the assembly also includes a screw that is threads into the side of the bolt and continues into the aperture of the bolt. The screw is used to push the rod toward the vertebral anchor so that the inside and outside ears of said clevis are pressed together and the clevis is tightened the vertebral anchor.

18 Claims, 8 Drawing Sheets

SPINAL IMPLANT CONNECTION ASSEMBLY

This invention relates to a spinal implant connection between a spinal rod and a vertebral anchor, and more particularly relates to a spinal implant connection with a clevis to attach to the vertebral anchor.

BACKGROUND

Spinal implant systems provide a rod for supporting the spine and for properly positioning components of the spine for various treatment purposes. Bolts, screws, and hooks are typically secured to the vertebrae for connection to the supporting rod. These vertebral anchors must frequently be positioned at various angles due the anatomical structure of the patient, the physiological problem being treated, and the preference of the physician. It is difficult to provide secure connections between the spinal support rod and these vertebral anchors at all the various angles that are required, especially where there are different distances between the rod and bolts and where these components are located at different heights on the patient.

One solution to this problem is shown in U.S. Pat. Nos. 5,643,263 and 5,885,285 to Simonson, the disclosures of which are specifically incorporated into this specification by reference. These patents describe a connection between a rod and a vertebral anchor, through which a surgeon may vary the angle between a spinal rod and the anchor to which the rod is attached. The connection is equipped with an interlocking set of washers that allow the surgeon to fix the desired angle between the anchor and the rod. In general, this system requires the surgeon in a typical installation to either sacrifice the capsule of the facet joint that may reside next to the connection, or elevate the connection above the facet joint and thereby raise the profile of the entire spinal implant system at that location. Occasionally, however, the surgeon may not wish to exercise either of these options in a particular surgery. Hence, an improvement over the device shown in these earlier patents would be a connection assembly that simultaneously minimizes the profile of the spinal implant system above the patient's spine without generally requiring the surgeon to sacrifice a facet joint that may reside next to a particular rod-to-vertebral-anchor connection assembly. The following invention is one solution to that need.

SUMMARY OF THE INVENTION

In one aspect, this invention is a connection assembly between a spinal implant rod and a vertebral anchor. The assembly has a bolt with a stop disposed near one end of the bolt and an aperture for receiving a portion of the spinal implant rod at the other end. The assembly also has a clevis. The clevis defines a bore to hold a portion of the vertebral anchor and the ears of the clevis have holes through which the bolt is located with the ears positioned between the stop and aperture of the bolt. The assembly also has a rod interface washer positioned over a portion of the bolt, between the aperture of the bolt and the inside ear of the clevis. The rod interface washer is partly movable between the aperture of the bolt and the clevis, but the washer is fixed against rotating in relation to the bolt. Finally, the assembly also includes a screw that threads into the side of the bolt and continues into the aperture of the bolt. The screw is used to push the rod toward the vertebral anchor so that the inside and outside ears of the clevis are pressed together and the clevis is tightened around the vertebral anchor.

Optionally, the inside ear of the clevis and the rod interface washer have mating male protrusions and female cavities on their surfaces such that, when pressed together, the protrusions and cavities engage to further prevent rotation of the clevis in relation to the rod interface washer. In this alternative design, the protrusions and cavities have multiple interlocking orientations so that the rod interface washer and the clevis can be interlocked in a plurality of fixed angles in relation to each other.

An object of this invention is to reduce the physical mass that is typically required to attach a spinal rod to a vertebral anchor.

An advantage of this invention is that the clevis allows a vertebral anchor to be placed closer to the spinal rod than prior art designs that also use a single means to allow the surgeon to secure both the anchor and the rod to the connection assembly in one tightening step.

A feature of this invention is that it allows the surgeon the option of lowering the profile of a spinal attachment system closer to the spine without requiring the surgeon to sacrifice the capsule of a facet joint that may reside next to the connection assembly. In other words, this invention allows the connection assembly to be placed in a position that is medial to the facet joint.

As used in this specification the term "clevis" is used in its ordinary and accustomed meaning that being—"(1): a fitting for attaching or suspending parts (as a cable to another structural member of a bridge or a hanger for supporting pipe) that consists usu, of a U-shaped piece of metal with the ends drilled to receive a pin or bolt (2): any of various connections in which one part is fitted between the forked ends of another and fastened by means of a bolt or pin passing through the forked ends." *Webster's Third New International Dictionary, Unabridged.*

DESCRIPTION OF THE PREFERRED EMBODIMENT

Specific language is used in the following description to publicly disclose the invention and to convey its principles to others. No limits on the breadth of the patent rights based simply on using specific language are intended. Also included are any alterations and modifications to the description that should normally occur to one of average skill in this technology.

Figure 1:
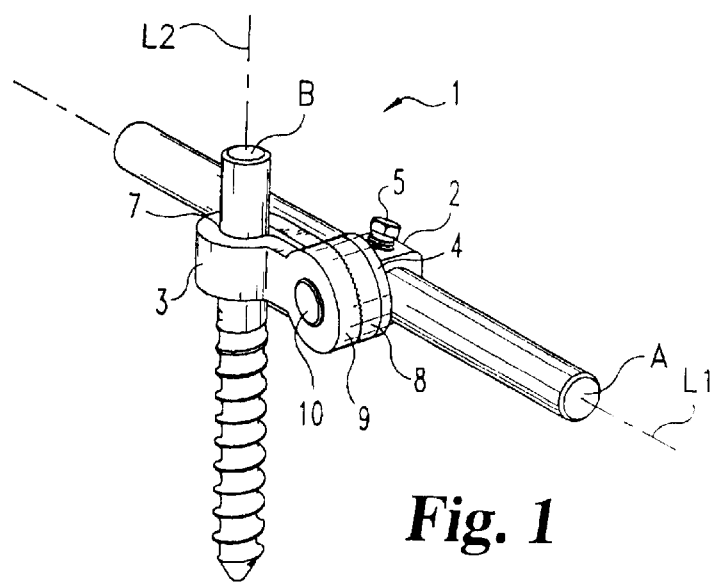
FIG. 1 is a perspective view of a connection assembly constructed pursuant to this invention.
Figure 2:
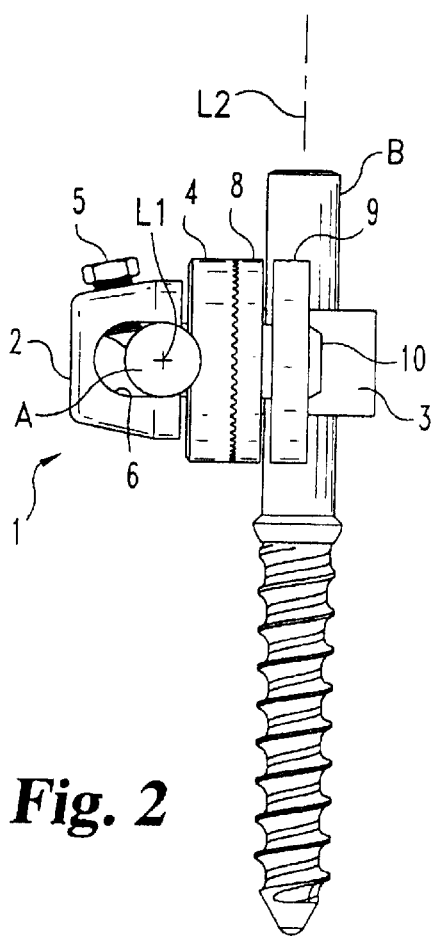
FIGS. 2 and 2A are end views of a connection assembly constructed pursuant to this invention.
Figure 3:
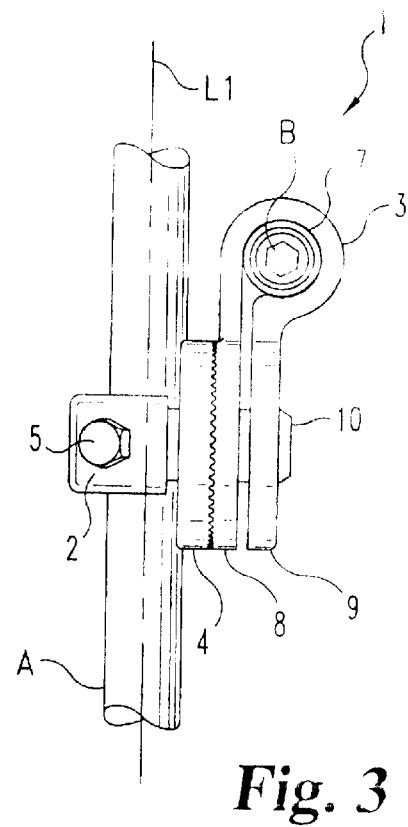
FIGS. 3 and 3A are top views of a connection assembly constructed pursuant to this invention.

A connection assembly 1 according to the invention is shown in FIGS. 1–3. Connection assembly 1 is shown attaching a spinal implant rod "A" with a longitudinal axis L1 to the shaft of a vertebral anchor "B" with the longitudinal axis L2. Connection assembly 1 includes a bolt 2, a clevis 3, a rod interface washer 4, and a set screw 5. Bolt 2 has an aperture 6 for receiving a rod in a spinal implant system. While a closed aperture is shown, it will nevertheless be understood that an open-sided aperture may also be used to permit top-loading of the connector rod. Set screw 5 is inserted through a threaded opening 15 in bolt 2 and into aperture 6 so as to allow set screw 5 to push against rod A. Clevis 3 has a bore 7 for receiving a vertebral anchor in a spinal implant system. Clevis 3 wraps around the shaft of vertebral anchor B and is simultaneously tightened when set screw 5 is tightened against rod A. It is contemplated that the shaft of B may be roughened and the interior of clevis 3 may be correspondingly roughened to increase friction between them. As set screw 5 pushes against rod A, rod A pushes against rod interface washer 4. This force pinches the ends 8 and 9 of clevis 3 together between rod interface washer 4 and stop 10, which tightens clevis 3 around vertebral anchor B. In this manner, set screw 5 acts as a compression member to tighten the connection assembly and achieve substantial fixation.

Figure 8:
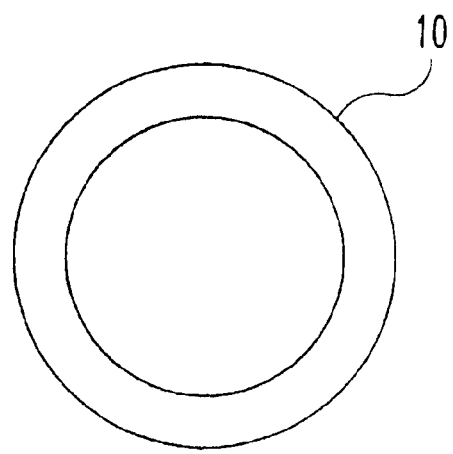
FIGS. 8 & 9 respectfully depict a stop in plan and elevational views constructed pursuant to this invention.
Figure 9:
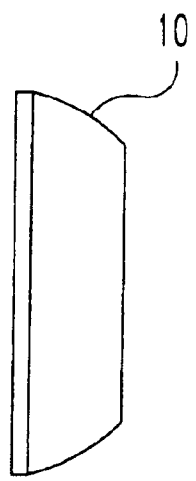

Details of bolt 2 are shown in FIGS. 4–7. Bolt 2 can be subdivided into bolt head portion 11, bolt shaft portion 12, washer seat portion 13 and washer stop portion 14. Threaded openings 15a & 15b, and aperture 6 reside in bolt head portion 11. Threaded openings 15a & 15b open into aperture 6 at an oblique angle A4 with respect to longitudinal axis L3 to allow set screw 5 (FIGS. 1–3) to force spinal rod A toward the distal end 16 of aperture 6. Bolt 2 is substantially symmetrical about longitudinal axis L3 such that threaded openings 15a and 15b are substantially mirror images. Bolt shaft portion 12 is generally cylindrical in shape and is sized to accept the eyes (items 17 and 18, FIG. 10) of clevis 3. Clevis 3 is then held on shaft portion 12 by attaching stop 10 (shown in isolation in FIGS. 8 & 9) to the end 19 of shaft portion 12, either by welding or some other suitable means. As an alternative, shaft portion 12 may include threads and stop 10 may be correspondingly threaded to be held in position. In this alternative design, stop 10 may be the compressive member utilized to tighten connection assembly 1.

Bolt 2 also preferably includes washer seat portion 13 and washer stop portion 14. A seat portion 13 that is substantially rectangular in cross-section is currently preferred, but washer seat portion 13 can be of any suitable shape that may interlock with a complementary shape in rod interface washer 4 (FIGS. 1–3) to prevent rod interface washer 4 from rotating in relation to bolt 2. As shown, washer stop 14 is generally provided by placing a raised edge in bolt head portion 11. Washer stop 14 prevents rod interface washer 4 from being inadvertently removed from connector assembly 1 during installation.

Figure 2A:
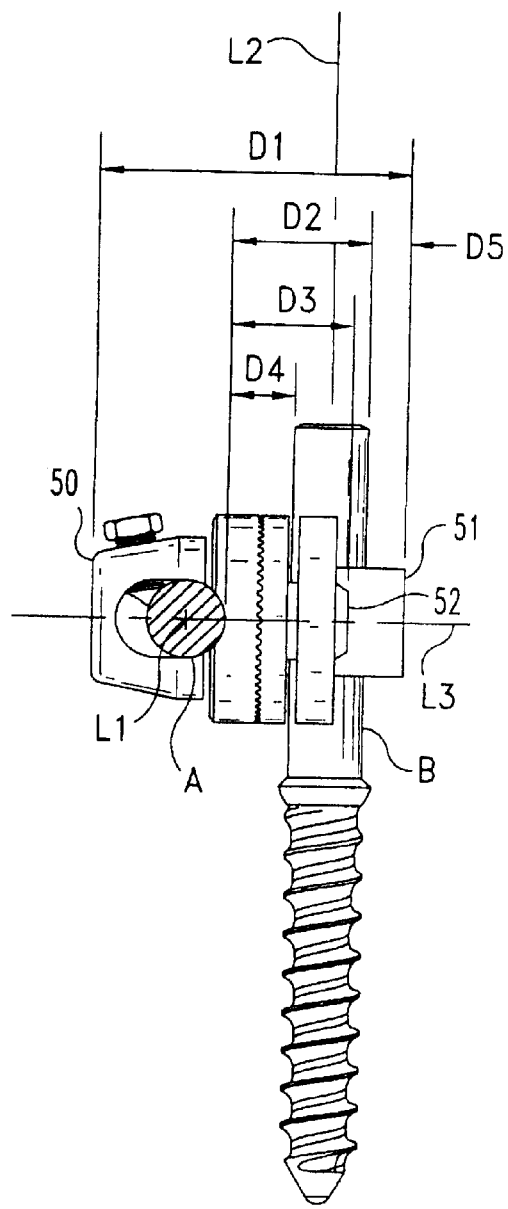
Figure 3A:
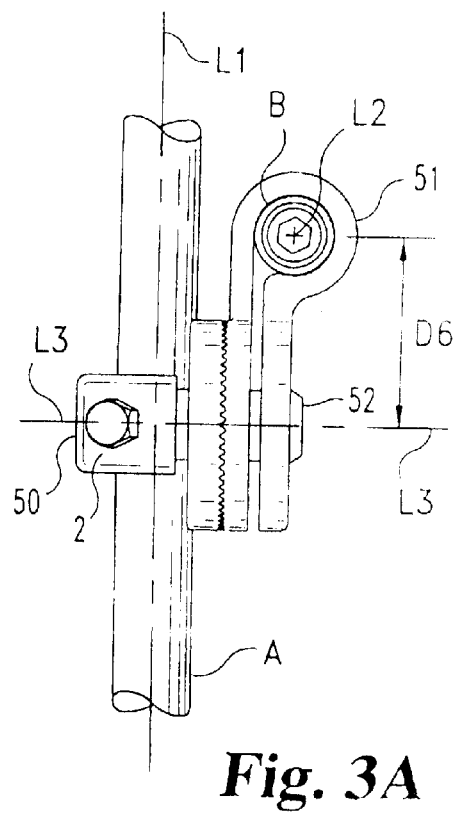
Figure 4:
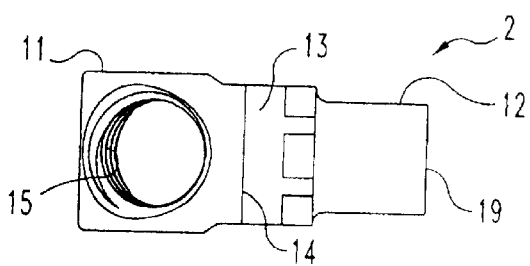
FIG. 4 is a top view of a bolt constructed pursuant to this invention.
Figure 5:
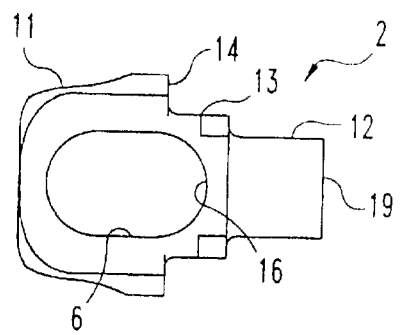
FIG. 5 is a side view of a bolt constructed pursuant to this invention.
Figure 6:
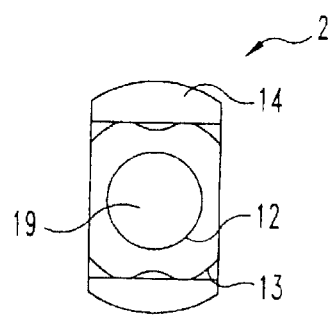
FIG. 6 is an end view of a bolt constructed pursuant to this invention.
Figure 7:
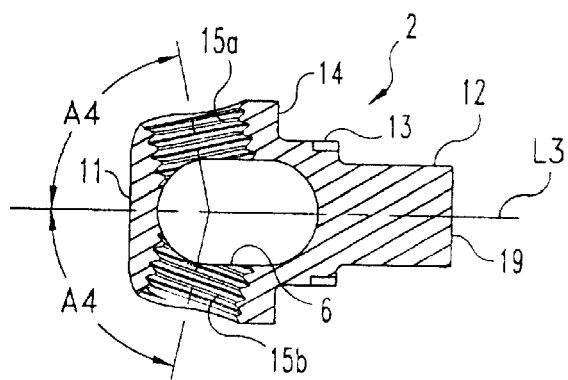
FIG. 7 is a cross-sectional view of a bolt constructed pursuant to this invention.

Referring to FIGS. 2A and 3A, additional characteristics of the preferred embodiment may be seen by contrasting several of connector assembly 1's relative dimensions. Dimension D1 is the overall width of connection assembly 1, measured from the most medial point 50 of connector assembly 1 to its most lateral point 51. Dimension D2 is the distance from the inside edge of rod A to the outside edge of vertebral anchor B, measured perpendicularly to L1. Dimension D3 is the distance from the inside edge of rod A to the most lateral end 52 of bolt 2, measured perpendicularly to L1. Dimension D4 is the distance from the inside edge of rod A to the inside edge of vertebral anchor B, measured perpendicularly to L1. Dimension D5 is the distance from the outside edge of vertebral anchor B to the most lateral point 51 of connector assembly 1. And dimension D6 is the distance from L2 to L3, measured parallel to L1.

Contrasting several of these dimensions, most notably D3 can be less than D2 in the present invention. In other words the outside edge 52 of bolt 2 does not need to extend beyond the outside edge of vertebral anchor B. Typically, most connectors place the bore to hold a vertebral anchor at the end of a bolt that typically holds the vertebral anchor to the rod, necessarily leaving a portion of the bolt extending past the vertebral anchor. An example of such a prior art design is shown in U.S. Pat. Nos. 5,643,263 and 5,885,285 to Simonson. But here, bolt 2 does not need to extend beyond anchor B, which would allow bolt 2 of connection 1 to be placed in more narrow passageways than connections of prior art designs.

Next it should be noted that the present invention allows dimension D4 to be shortened as the surgeon may desire, reducing the overall width D1 of the connector assembly. In other words and referring also to FIGS. 13 & 14, the present design allows D4 to be shortened by placing the bore 7 of clevis 3 in a position that is closer to rod A. For example, clevis 3 shown in FIG. 14 could conceivably place vertebral anchor B so close to rod A that only the width of clevis 3 around bore 7 would separate vertebral anchor B from rod A.

Finally, the present design also allows vertebral anchor B to be laterally offset a distance D6 from the longitudinal axis L3 of bolt 2, allowing bolt 2 and its connection to rod A to lie in a different transverse plane on the patient than vertebral anchor B would lie. Most prior art designs such as U.S. Pat. Nos. 5,643,263 and 5,885,285 to Simonson place the bore to hold vertebral anchor B in the same transverse plane as the connection to rod A. In other words, vertebral anchor B is usually situated in line with the longitudinal axis of the structure, usually a bolt, that holds the vertebral anchor B and rod A together. Here, however, the present invention allows bolt 2 to be placed in one transverse plane (in one longitudinal location along rod A) and vertebral anchor B to be placed in another transverse plane (or another longitudinal location along rod A). Thusly situated, bolt 2 is separated from vertebral anchor B by a distance D6, measured longitudinally along rod A. Moreover, D6 can be larger than D4, readily allowing bolt 2 to be placed in one longitudinal position on the spine and vertebral anchor B to be placed in another position, above or below bolt 2. Located in this fashion, the surgeon can place the connector assembly of the present invention in a location that avoids interfering with the facet joints of the patient's spine.

Figure 10:
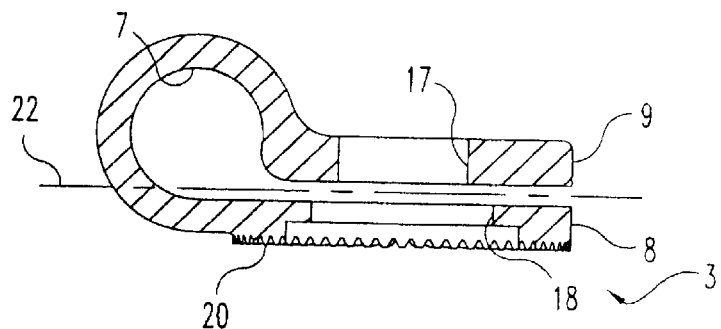
FIG. 10 is a cross-sectional view of clevis constructed pursuant to this invention.
Figure 11:
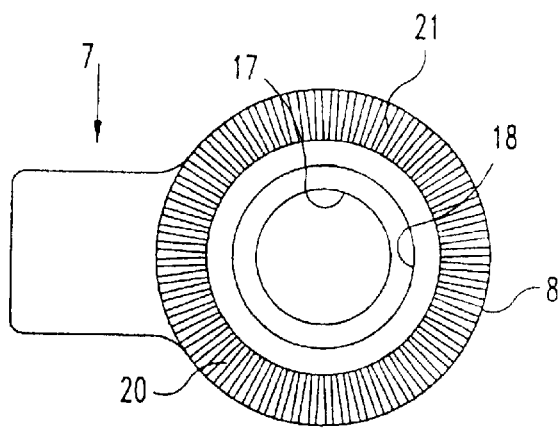
FIG. 11 is an end view of a clevis constructed pursuant to this invention.
Figure 12:
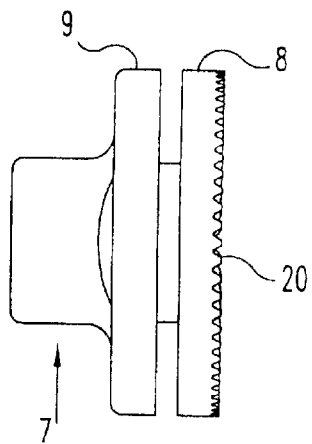
FIG. 12 is a side view of a clevis constructed pursuant to this invention.
Figure 15:
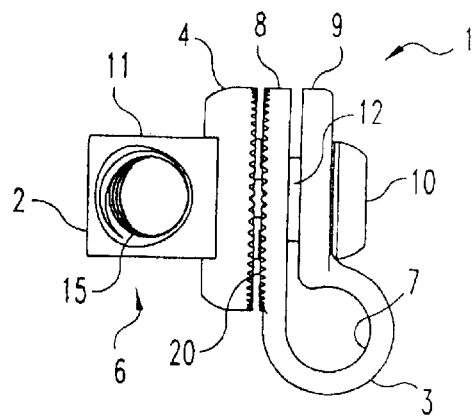
FIGS. 15, 16 & 17 are respectively top, side, and cross-sectional views of a connection assembly constructed pursuant to this invention.

Details of clevis 3 are shown in FIGS. 10–12. Clevis 3 includes a bore 7, a proximal ear 8 or end 8 and a distal ear 9 or end 9. Proximal ear 8 has an eye 18 and distal ear 9 has an eye 17. As previously presented, bolt 5 attaches to clevis 3 by placing the shaft portion of bolt 5 through eyes 17 and 18 and then attaching end 10 (FIG. 15). The proximal ear 8 also includes a connection surface 20. Connection surface 20 preferably includes structure for facilitating the engagement of clevis 3 against rotational movement relative to rod interface washer 4. This engagement structure is preferably a plurality of variable angle ridges 21 that radiate from the rotational center of clevis 3. In other words, the structure is a set of interlocking teeth that can generally be characterized as male protrusions and complementary female cavities.

Figure 13:
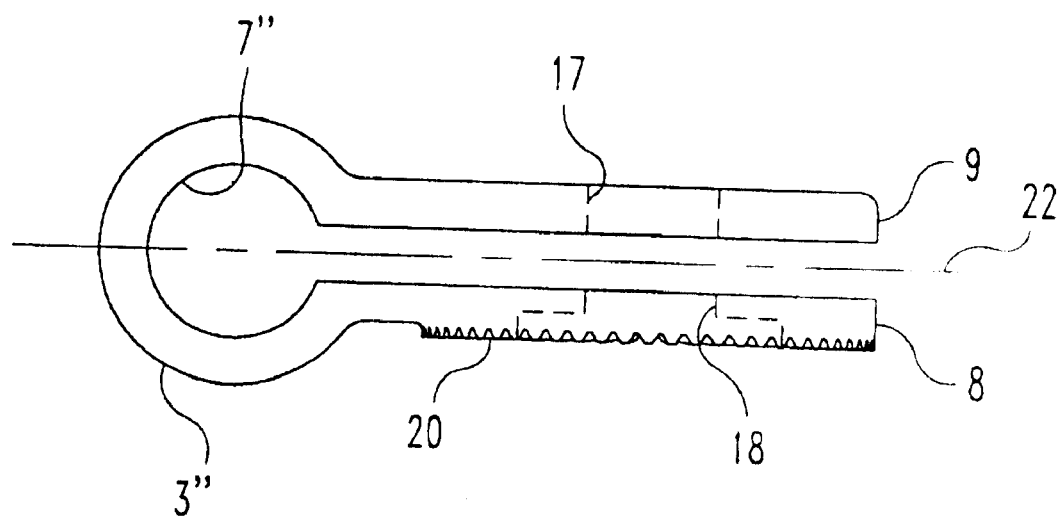
FIG. 13 is a side view of one alternative embodiment of a clevis constructed pursuant to this invention.
Figure 14:
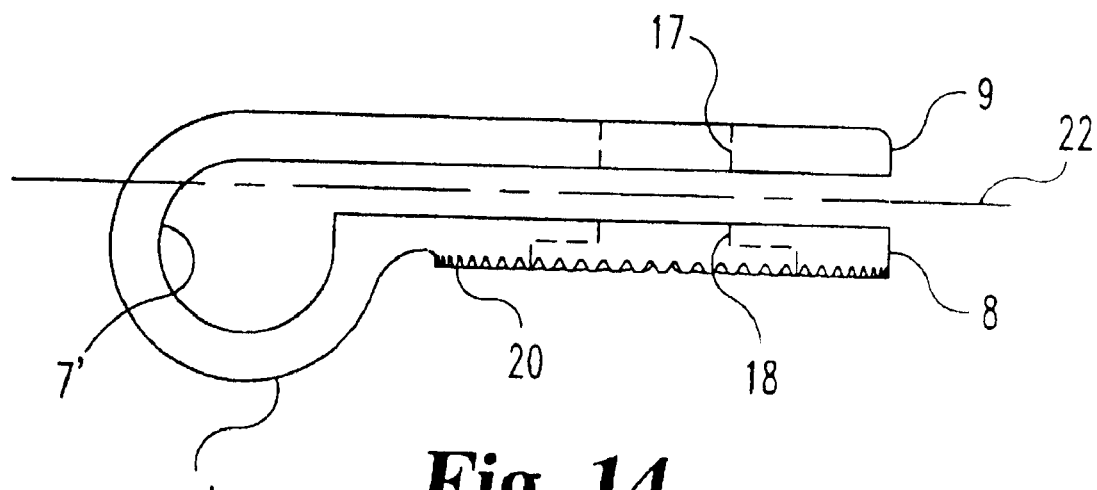
FIG. 14 is a side view of a second alternative embodiment of a clevis constructed pursuant to this invention.

Referring to FIGS. 10, 13 and 14; bore 7 of clevis 3 may assume various orientations in relation to the centerline 22 of clevis 3. FIG. 10 depicts bore 7 offset from centerline 22 toward the stop (not shown) of bolt 2. Optionally, bore 7' can be offset from centerline 22' toward the aperture (not shown) of bolt 2, as shown in alternative clevis 3' of FIG. 14, or bore 7' can be placed in the same plane as centerline 22", as shown in alternative clevis 3" of FIG. 13. It being understood that the alternative clevis designs may permit even smaller total width of connection assembly by bringing the vertebral anchor closer to the rod.

Figure 18:
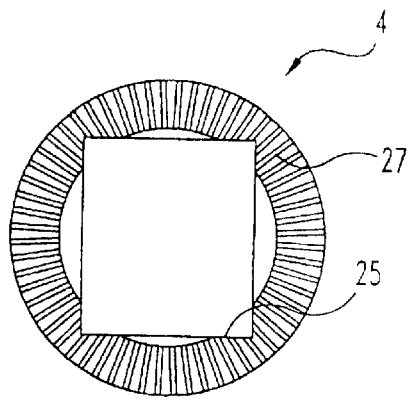
FIGS. 18, 19 & 20 are respectively end, side, and top views of a rod interface washer constructed pursuant to this invention.
Figure 19:
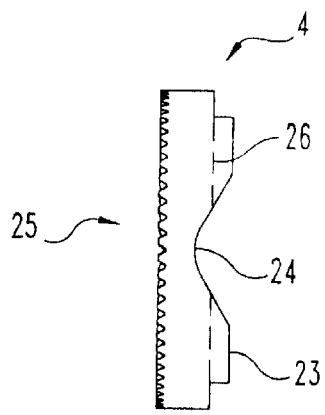
Figure 20:
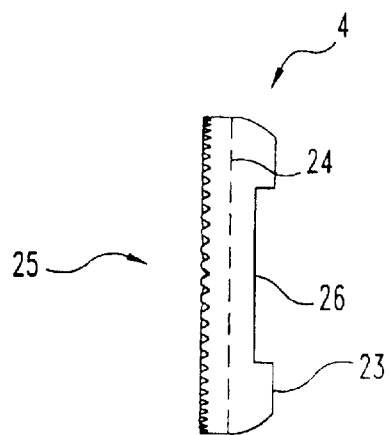

Details of rod interface washer 4 are shown in FIGS. 18–20. Rod interface washer 4 can be any of several suitable shapes, including the circle that is depicted. One surface 23 of the rod interface washer 4 has an engagement surface, which preferably includes an engagement groove 24 that accepts a cylindrical spinal implant rod (such as rod A in FIGS. 1–3). Engagement groove 24 preferably runs across the entire face of surface 23. Rod interface washer 4 also has a central opening 25 that corresponds to the crosssectional shape of previously presented washer seat portion 13 in bolt 2. In the currently preferred embodiment, both washer seat portion 13 and opening 25 are substantially square. Although, this shape could vary from many possible shapes that would similarly prevent rod interface washer from rotating in respect to bolt 2. To assist in this regard, it is also preferable that rod interface washer have a guide groove 26 to accept bolt head portion 11 of bolt 2 to further lock bolt 2 and rod interface washer 4 together. In this regard it should be noted that guide groove 26 and engagement groove 24 are preferably placed in such a manner that orients aperture 6 substantially parallel to groove 24. This placement helps insure that a spinal rod (item A in FIGS. 1–3) will be held in the connector assembly in a direction that is substantially perpendicular to bolt 2, and in turn, also substantially perpendicular to set screw 5.

Rod interface washer 4 also includes connection surface 27. Connection surface 27 preferably includes structure for facilitating the engagement of rod interface washer against rotational movement relative to clevis 3. This engagement structure is preferably a plurality of variable angle ridges 28 that radiate from the rotational center of rod engagement washer 4 as that previously described on clevis 3. Variable angle ridges 28 are sized to mate with the similar variable angle ridges 21 on clevis 3. Referring to FIGS. 11 and 18, both sets of ridges consist of alternating male protrusions and female cavities. Hence, once placed together, these interlocking ridges prevent rod engagement washer 4 from rotating in respect to clevis 3. And although radiating ridges are shown to facilitate the fixation of these two parts, it is also contemplated that other structures could serve this function. For example, it is also contemplated that one could use any number of interlocking male and female structures such as rounded bumps or knurling and mating cavities. The locking engagement of connection surface 20 with connection surface 27 may occur at any of a plurality of angles. More specifically, the angle between longitudinal axis L1 of the vertebral anchor and longitudinal axis L2 of the rod may be adjusted to meet the requirements of the patient's anatomy.

Figure 16:
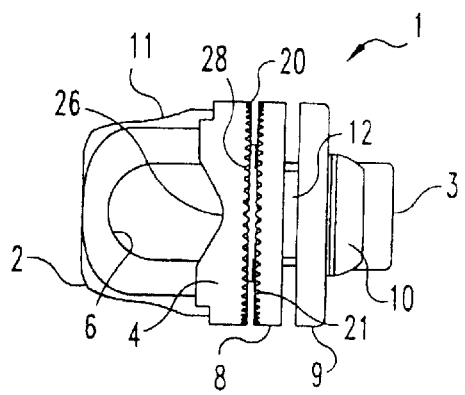
Figure 17:
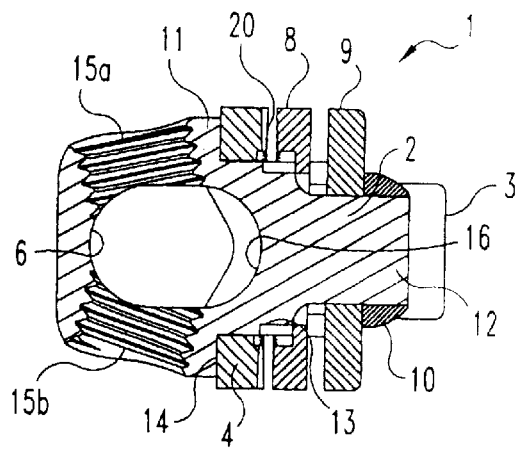

The rotatable connection assembly of this invention is again depicted in FIGS. 15–17, less set screw 5, which has been removed for clarity along with rod A and vertebral anchor B. The device is used by placing a spinal rod through aperture 6 in bolt 2. The post of a vertebral anchor is then located in bore 7 of clevis 3 and the variable angle ridges 20 on the rod interface washer are interlocked with the variable angle ridges 28 on clevis 3 as the surgeon desires. Thusly situated, the assembly is then tightened by threading set screw 5 into either of the threaded openings 15 of bolt 2. Upon entering aperture 6, set screw 5 contacts the spinal rod and forces the spinal rod toward interface washer 4. The spinal rod then contacts rod interface washer 4, and preferably engages groove 24. As one continues turning set screw 5, rod interface washer presses ears 8 and 9 of clevis 3 against stop 10. This action forces ears 8 and 9 together, which in turn, tighten clevis 3 around the post of the vertebral anchor. The variable angle surfaces, item 20 on clevis 3 and item 27 on rod interface washer 4, engage each other and prevent rod interface washer 4 from rotating in relation to clevis 3, which further locks clevis 3 in relation to bolt 2 because rod interface washer 4 cannot rotate in relation to bolt 2. Adjustments can be made by loosening set screw 5 then re-tightening the set screw when the preferred position has been located.

While the invention has been illustrated and described in detail, this is to be considered as illustrative and not restrictive of the patent rights. The reader should understand that only the preferred embodiments have been presented and all changes and modifications that come within the spirit of the invention are included if the following claims or the legal equivalent of claims describes them.

I claim:

1. An apparatus for maintaining vertebra in a desired relationship, comprising:

a rod having a first longitudinal axis;

a vertebral anchor having a second longitudinal axis generally perpendicular to the longitudinal axis of said rod;

a connection assembly, said connection assembly including a bolt and a clevis, said bolt having a first channel for receiving said rod and a head defining an aperture, said clevis joined to said bolt, said clevis having a second channel for receiving said vertebral anchor;

wherein said connection assembly includes a compression member threadably received by the head of said bolt and extending within the aperture to urge said rod toward said vertebral anchor to thereby fix the relative position of said rod to said vertebral anchor.

2. The apparatus of claim 1 wherein said clevis is one piece.

3. The apparatus of claim 1, wherein said clevis engages a non-threaded shaft of said vertebral anchor.

4. The apparatus of claim 1 wherein said bolt engages said rod at a first longitudinal position, and said vertebral anchor is spaced from said first longitudinal position along the first longitudinal axis.

5. The apparatus of claim 1 which further comprises a rod interface washer positioned over a portion of said bolt, wherein said clevis has first and second overlapping ears, one said ear of said clevis includes a first surface and said rod interface washer includes a second surface facing the first surface, one of the first or second surfaces having a plurality of male protrusions which engage with a plurality of female cavities on the other of the first or second surfaces, whereby tightening of said compression member results in alignment of said clevis relative to said rod interface washer at one of a corresponding plurality of discrete angles.

6. An apparatus for maintaining vertebra in a desired relationship, comprising:

a rod having a first longitudinal axis;

a vertebral anchor having an outer diameter and a second longitudinal axis generally perpendicular to the longitudinal axis of said rod; and a connection assembly, said connection assembly including a bolt and a clevis, said bolt having a head and a shaft, said bolt having a first channel for receiving said rod and a portion with a third longitudinal axis, said clevis joined to said bolt, said clevis having first and second overlapping ears and a centerline therebetween, said clevis having a second channel for receiving said vertebral anchor, said second channel offset from said third longitudinal axis, said second channel being laterally offset from the centerline;

wherein said rod is spaced from said vertebral anchor by a first distance that is perpendicular to a first longitudinal axis, said rod is spaced from the free end of the shaft of said bolt by a second distance that is perpendicular to the first longitudinal axis, and the second distance is less than the sum of the first distance added to the outer diameter of the anchor.

7. The apparatus of claim 6 which further comprises a rod interface washer positioned over a portion of the bolt proximate the inside ear of said clevis and a compression member threadably engaged to said bolt;

wherein one said ear of said clevis includes a first surface and said rod interface washer includes a second surface facing the first surface, one of the first or second surfaces having a plurality of male protrusions which engage with a plurality of female cavities on the other of the first or second surfaces, whereby tightening of said compression member results in alignment of said clevis relative to said rod interface washer at one of a corresponding plurality of discrete angles.

8. The apparatus of claim 7, wherein said compression member is a set screw received in an internally threaded opening in said bolt, said set screw substantially aligned with said third axis.

9. The apparatus of claim 6, wherein said clevis is one piece.

10. The apparatus of claim 6, wherein said clevis engages a non-threaded shaft of said vertebral anchor.

11. The apparatus of claim 6, wherein said rod is spaced from said vertebral anchor by a first distance that is perpendicular to the first longitudinal axis, the second longitudinal axis is spaced from the third longitudinal axis by a second distance, and said second distance greater than said first distance.

12. An apparatus for maintaining vertebra in a desired relationship, comprising:

a rod having a first longitudinal axis;

a vertebral anchor having a second longitudinal axis generally perpendicular to the longitudinal axis of said rod;

a connection assembly, said connection assembly including a bolt and a clevis, said bolt having a first channel for receiving said rod and a portion with a third longitudinal axis, said clevis joined to said bolt, said clevis having a second channel for receiving said vertebral anchor, said second channel offset from said third longitudinal axis;

wherein said bolt engages said rod at a first longitudinal position, and said vertebral anchor is spaced from said first longitudinal position along the first longitudinal axis, said connection assembly includes a compression member to tighten said connection assembly and thereby fix the relative position of said rod to said vertebral anchor;

wherein said compression member is a set screw received in an internally threaded opening in said bolt, said set screw substantially aligned with said third axis;

wherein said rod is spaced from said vertebral anchor by a first distance that is perpendicular to the first longitudinal axis and the second longitudinal axis is spaced from the third longitudinal axis by a second distance, said second distance greater than said first distance.

13. An apparatus for maintaining vertebra in a desired relationship, comprising:

a rod having a first longitudinal axis;

a vertebral anchor having a second longitudinal axis generally perpendicular to the longitudinal axis of said rod;

a connection assembly, said connection assembly including a bolt and a clevis, said bolt having a first channel for receiving said rod and a portion with a third longitudinal axis, said clevis joined to said bolt, said clevis having a second channel for receiving said vertebral anchor, said second channel offset from said third longitudinal axis;

wherein said bolt engages said rod at a first longitudinal position, and said vertebral anchor is spaced from said first longitudinal position along the first longitudinal axis, said connection assembly includes a compression member to tighten said connection assembly and thereby fix the relative position of said rod to said vertebral anchor;

wherein said compression member is a set screw received in an internally threaded opening in said bolt, said set screw substantially aligned with said third axis;

wherein said clevis engages a non-threaded shaft of said vertebral anchor.

14. An apparatus for maintaining vertebra in a desired relationship, comprising:

a rod having a first longitudinal axis;

a vertebral anchor having a second longitudinal axis generally perpendicular to the longitudinal axis of said rod;

a connection assembly, said connection assembly including a bolt and a clevis, said bolt having a first channel for receiving said rod and a portion with a third longitudinal axis, said clevis joined to said bolt, said clevis having a second channel for receiving said vertebral anchor, said second channel offset from said third longitudinal axis;

wherein said clevis is one piece, said connection assembly includes a compression member to tighten said connection assembly and thereby fix the relative position of said rod to said vertebral anchor;

wherein said compression member is a set screw received in an internally threaded opening in said bolt, said set screw substantially aligned with said third axis;

wherein said rod is spaced from said vertebral anchor by a first distance that is perpendicular to the first longitudinal axis and the second longitudinal axis is spaced from the third longitudinal axis by a second distance, said second distance greater than said first distance.

15. An apparatus for maintaining vertebra in a desired relationship, comprising:

a rod having a first longitudinal axis;

a vertebral anchor having a second longitudinal axis generally perpendicular to the longitudinal axis of said rod;

a connection assembly, said connection assembly including a bolt and a clevis, said bolt having a first channel for receiving said rod and a portion with a third longitudinal axis, said clevis joined to said bolt, said clevis having a second channel for receiving said vertebral anchor, said second channel offset from said third longitudinal axis;

wherein said clevis is one piece, said connection assembly includes a compression member to tighten said connection assembly and thereby fix the relative position of said rod to said vertebral anchor;

wherein said compression member is a set screw received in an internally threaded opening in said bolt, said set screw substantially aligned with said third axis;

wherein said clevis engages a non-threaded shaft of said vertebral anchor.

16. An apparatus for maintaining vertebra in a desired relationship, comprising:

a rod having a first longitudinal axis;

a vertebral anchor having a second longitudinal axis generally perpendicular to the longitudinal axis of said rod;

a connection assembly, said connection assembly including a bolt and a clevis, said bolt having a first channel for receiving said rod and a portion with a third longitudinal axis, said clevis joined to said bolt, said clevis having a second channel for receiving said vertebral anchor, said second channel offset from said third longitudinal axis;

wherein said connection assembly includes a compression member to tighten said connection assembly and thereby fix the relative position of said rod to said vertebral anchor, wherein said compression member is a set screw received in an internally threaded opening in said bolt, said set screw substantially aligned with said third axis;

wherein said rod is spaced from said vertebral anchor by a first distance that is perpendicular to the first longitudinal axis and the second longitudinal axis is spaced from the third longitudinal axis by a second distance, said second distance greater than said first distance.

17. An apparatus for maintaining vertebra in a desired relationship, comprising:

a rod having a first longitudinal axis;

a vertebral anchor having a second longitudinal axis generally perpendicular to the longitudinal axis of said rod;

a connection assembly, said connection assembly including a bolt and a clevis, said bolt having a first channel for receiving said rod and a portion with a third longitudinal axis, said clevis joined to said bolt, said clevis having a second channel for receiving said vertebral anchor, said second channel offset from said third longitudinal axis;

wherein said connection assembly includes a compression member to tighten said connection assembly and thereby fix the relative position of said rod to said vertebral anchor, wherein said compression member is a set screw received in an internally threaded opening in said bolt, said set screw substantially aligned with said third axis;

wherein said clevis engages a non-threaded shaft of said vertebral anchor.

18. An apparatus for maintaining vertebra in a desired relationship, comprising:

a rod having a first longitudinal axis;

a vertebral anchor having a second longitudinal axis generally perpendicular to the longitudinal axis of said rod; and a connection assembly, said connection assembly including a bolt and a clevis, said bolt having a first channel for receiving said rod, said clevis joined to said bolt, said clevis having a second channel for receiving said vertebral anchor;

wherein said bolt engages said rod at a first longitudinal position, said vertebral anchor spaced from said first longitudinal position along the first longitudinal axis, said connection assembly includes a compression member to tighten said connection assembly and thereby fix the relative position of said rod to said vertebral anchor, wherein said compression member is a set screw received in an internally threaded opening in said bolt;

wherein said clevis engages a non-threaded shaft of said vertebral anchor.

* * * * *

UNITED STATES PATENT AND TRADEMARK OFFICE
CERTIFICATE OF CORRECTION

PATENT NO.     : 6,562,038 B1
DATED          : May 13, 2003
INVENTOR(S)    : Matthew M. Morrison It is certified that error appears in the above-identified patent and that said Letters Patent is hereby corrected as shown below:

<u>Column 7,</u>
Line 26, delete the word "a" appearing after the word "to" and replace with -- the --.

Signed and Sealed this

Thirteenth Day of July, 2004

JON W. DUDAS
*Acting Director of the United States Patent and Trademark Office*